US006790859B2

(12) United States Patent
Wagle et al.

(10) Patent No.: US 6,790,859 B2
(45) Date of Patent: *Sep. 14, 2004

(54) REVERSING ADVANCED GLYCOSYLATION CROSS-LINKS USING HETEROCYCLIC-SUBSTITUTED THIAZOLIUM COMPOUNDS

(75) Inventors: Dilip R. Wagle, Nanuet, NY (US); Sheng-Ding Fang, Mahwah, NJ (US); Taikyun Rho, Saddle Brook, NJ (US); John J. Egan, NY, NY (US); Sara Vasan, Yonkers, NY (US); Peter Ulrich, Old Tappan, NJ (US); Anthony Cerami, New York, NY (US)

(73) Assignee: Alteon Incorporated, Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/348,378

(22) Filed: Jan. 21, 2003

(65) Prior Publication Data

US 2003/0176417 A1 Sep. 18, 2003

Related U.S. Application Data

(62) Division of application No. 10/003,514, filed on Oct. 23, 2001, now abandoned, which is a division of application No. 09/644,024, filed on Aug. 23, 2000, now Pat. No. 6,319,934, which is a continuation of application No. 09/189,200, filed on Nov. 10, 1998, now Pat. No. 6,121,300.

(51) Int. Cl.[7] ............................................. A61K 31/425
(52) U.S. Cl. ...................................................... 514/365
(58) Field of Search ............................................ 514/365

(56) References Cited

U.S. PATENT DOCUMENTS

| 4,558,046 A | 12/1985 | Doria et al. |
| 4,609,660 A | 9/1986 | Doria et al. |
| 4,609,670 A | 9/1986 | Dominianni et al. |
| 4,683,312 A | 7/1987 | Dominianni et al. |
| 4,692,450 A | 9/1987 | Cassal |
| 4,886,814 A | 12/1989 | Reiffen et al. |
| 4,956,370 A | 9/1990 | Ippen et al. |
| 5,128,351 A | 7/1992 | Wissner |
| 5,219,852 A | 6/1993 | Reiffen et al. |
| 5,225,425 A | 7/1993 | Wissner |
| 5,230,998 A | 7/1993 | Neurath et al. |
| 5,240,950 A | 8/1993 | Sohda et al. |
| 5,266,578 A | 11/1993 | Raddatz et al. |
| 5,302,608 A | 4/1994 | Sohda et al. |
| 5,350,759 A | 9/1994 | Wissner |
| 5,432,189 A | 7/1995 | Wissner |
| 5,449,680 A | 9/1995 | Solomon et al. |
| 5,457,205 A | 10/1995 | Reiffen et al. |
| 5,500,436 A | 3/1996 | Schonafinger et al. |
| 5,532,257 A | 7/1996 | Hase et al. |
| 5,604,225 A | 2/1997 | Reiffen et al. |
| 5,656,261 A | 8/1997 | Cerami et al. ................ 424/53 |
| 5,665,748 A | 9/1997 | Sohda et al. |
| 5,679,704 A | 10/1997 | Schonafinger et al. |
| 5,700,819 A | 12/1997 | Aotsuka et al. |
| 6,121,300 A * | 9/2000 | Wagle et al. ................. 51/365 |
| 6,319,934 B1 * | 11/2001 | Wagle et al. ................. 51/365 |

FOREIGN PATENT DOCUMENTS

| CA | 2074568 | 1/1993 |
| DE | 42 18 159 A1 | 12/1993 |
| DE | 43 41 526 A1 | 6/1995 |
| EP | 0 167 139 A1 | 1/1986 |
| EP | 0 170 073 A1 | 2/1986 |
| EP | 0 614 886 A1 | 9/1994 |
| JP | 60-184038 | 9/1985 |

OTHER PUBLICATIONS

Tamura et al., Novel Syntheses of Thiazolo [3,2–b]–s–triazoles, J. Heterocyclic Chem. 10: 947–951, 1972.

Potts et al., Cycloaddition of N–iminothiazolium Ylides with Acetylenic Dipolarophiles. Formation of Pyrazoles, J. Org. Chem. vol. 42, No. 9, 1977 pp. 1648–1649.

Potts et al., Bridgehead Nitrogen Systems. X. Cycloadditions with Thiazolium N–Ylides, J. Org. Chem. vol. No. 2, pp. 187–191, 1976.

Archer et al., An Attempt to Apply Lethal Synthesis to the Design of Chemotherapeutic Agents. Fluorinated 5B–(Hydoxyethyl)–4–methylides, J. of Medicinal Chemistry, vol. 22, No. 3, 1979.

Tsuge et al., Chemistry Letters, Formation of Novel Cage Compounds Via Endo–[3 + 2] Cycloadducts Between Thiazolium N–Methylides and Methylenecyclopropenes, vol. 5, pp. 711–714, 1982.

Hirano et al., New Aspects of the 1,3–Dipolar Cycloaddition of Thiazolium N–Imines with Dimethyl Acetylenedicarboxylate (DMAD), Chem. Pharm. Bull., vol. 32, 1984.

Dominianni et al., J. of Medicinal Chemistry, Oral Hypoglycemic Agents. Discovery and Structure—Activity Relationships of Phenacylimidazolium Halides, 32:2301–2306, 1989.

(List continued on next page.)

Primary Examiner—Deborah C. Lambkin
(74) Attorney, Agent, or Firm—Mintz, Levin, Cohn, Ferris, Glovsky and Popeo, PC.; Ivor R. Elrifi; Heidi A. Erlacher

(57) ABSTRACT

The present invention relates to compositions and methods for reversing advanced glycosylation end product-mediated cross-linking and protein aging. Accordingly, compositions are described which comprise thiazolium compounds substituted with heterocyclic groups which are capable of reversing the formation of advanced glycosylation end product cross-links. Both industrial and therapeutic applications for the invention are disclosed, as food spoilage and animal protein aging can be treated. Such compounds have particular application in the treatment of protein aging such as is responsible for the complications of aging and diabetes.

21 Claims, No Drawings

OTHER PUBLICATIONS

Gandasegui, MT et al., Heterocycles, Synthesis of New Disubstituted Azolium Ylides, 31:(10): 1801–9, 1990.

Aldrich Catalog Handbook of Fine Chemicals, 1992–1993, pp. 134, 257, 505, 594.

Singh et al., Tetrahedron, Aqueous Base Induced Selective Transformations of 3–(2–OXOALKYL) Thiazolium Cations, 48:(22) 4545–50, 1992.

Kumar et al., J. Medicinal Chemistry, Synthesis of 2,4–Disubstituted Thiazoles and Selenazoles as Potential Antitumor and Antifilarial Agents: 1. Methyl 4–(Isothiocyanatometyl) thiazole–2–carbamates, –selenazole–2–carbamtes, and Related Derivatives, 36:3843–3848, 1993.

Hays et al., Journal of Pharmaceutical Sciences, Substituted 2–Benzothiazolamines as Sodium Flux Inhibitors: Quantitive Structure–Activity Relationships and Anticonvulsant Activity, vol. 83, No. 10, 1994.

Tsuge Bull. Chem. Soc. Japan 58, 3137–57, 1985.

Wolffenbuttel, et al., *Proc. Natl. Acad. Sci. USA*, 95(8):4630–4634 (1998).

Supplementary European Search Report for EP 99 97 1712, mailing date: Feb. 23, 2004.

* cited by examiner

REVERSING ADVANCED GLYCOSYLATION CROSS-LINKS USING HETEROCYCLIC-SUBSTITUTED THIAZOLIUM COMPOUNDS

This application is a Divisional of U.S. application Ser. No. 10/003,514 filed Oct. 23, 2001, now abandoned, which is a Divisional of U.S. application Ser. No. 09/644,024 filed Aug. 23, 2000, now known as U.S. Pat. No. 6,319,934, which is a Continuation of U.S. application Ser. No. 09/189/200 filed Nov. 10, 1998, now known as U.S. Pat. No. 6,121,300.

BACKGROUND OF THE INVENTION

The present invention relates generally to the aging of proteins resulting from their reaction with glucose and other reducing sugars, and more particularly to the reversing or cleavage of cross-links formed as a consequence of the formation of advanced glycosylation (glycation) end products.

This application claims the priority of U.S. application Ser. No. 09/189,200 filed Nov. 10, 1998 (now U.S. Pat. No. 6,121,300 issued Sep. 19, 2000) and U.S. application Ser. No. 09/644,024 filed Aug. 23, 2000 (now U.S. Pat. No. 6,319,934 issued Nov. 20, 2001) and U.S. application Ser. No. 10/003,514 filed Oct. 23, 2001 now abandoned.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Further studies have suggested that stored and heat treated foods undergo nonenzymatic browning as a result of the reaction between glucose and the polypeptide chain, and that the proteins are resultantly cross-linked and correspondingly exhibit decreased bioavailability. As described in copending application Ser. No. 08/588,249, incorporated herein by reference, these reactions have a parallel in vivo, and have been found to occur with a variety of other body proteins, such as lens crystallins, collagen and nerve proteins. These reactions are accelerated in the presence of elevated glucose levels, as occur in individuals with diabetes mellitus, but still occur in vivo at normal glucose levels. Termed advanced glycosylation (or glycation) end products (AGEs), the cross-linked products involving structural and other proteins within the body leads not only to aberrant physico-chemical properties of, for example, connective tissue, but also results in the formation of new chemical structures which are recognized by specific receptors on various cell types and as a consequence of their recognition, initiate pathogenetic mechanisms leading to the complications of diabetes and aging.

Several successful therapeutic approaches have been achieved based upon intervening in the accumulation of AGEs in vivo. One approach, exemplified in U.S. Pat. No. 4,758,583, incorporated herein by reference, concerns the inhibition of the formation of AGEs from its precursors, by the administration of agents such as aminoguanidine and related compounds. By reacting with an early glycosylation product that results from the original reaction between the target protein and glucose, these agents block the formation of AGEs and further formation of AGEs and cross-links in tissues is inhibited. Efficacy of this approach has been demonstrated in numerous animal models of diabetes and aging, including positive effects on macrovascular, renal, retinal, and neural pathology. These data have been reviewed by Vlassara et al., 1994, "Biology of Diseases. Pathogenic effects of advanced glycosylation: biochemical, biologic and clinical implications for diabetes and aging," Laboratory Investigation 70:138–151; Brownlee, 1995, "The pathological implications of protein glycation," Clin. Invest. Med., 18:275–281; and Brownlee, 1995, "Advanced protein glycosylation in diabetes and aging," Ann. Rev. Med. 46:223–34.

In another pharmacological approach to controlling levels of AGEs in tissues, especially in those tissues in which AGE cross-links have already accumulated to levels which are responsible for subclinical or clinical pathology, administration of agents that reverse or break AGE cross-links has proven successful. As described in U.S. Pat. No. 5,656,261 and copending U.S. application Ser. Nos. 08/588,249 and 08/848,776, all of which are incorporated herein by reference in their entireties, agents and methods are disclosed which reverse (also termed cleave or break) existing AGE cross-links in vitro and in vivo. Studies demonstrate positive effects of such agents on cardiovascular complications related to aging which are accelerated in experimental diabetes (see Wolffenbuttel et al., 1998, "Breakers of Advanced Glycation End Products Restores Large Artery Properties in Experimental Diabetes," Proc. Nat. Acad. Sci. U.S.A. 95:4630–4634). In these studies, rats diabetic for 9 weeks followed by 1 to 3 weeks administration of an AGE breaker compound resulted in reversal of diabetes-induced increases in large artery stiffness. Parameters that were improved included cardiac output, peripheral resistance, systemic arterial compliance, input impedance of the aorta, and compliance of the carotid artery.

It is toward the identification of additional agents capable of reversing AGE cross-links that the present invention is directed.

SUMMARY OF THE INVENTION

In accordance with the present invention, compounds and method are disclosed for reversing AGE cross-linking. AGE cross-linking caused by other reactive sugars present in vivo or in foodstuffs, including ribose, galactose and fructose would also be reversed by the methods and compositions of the present invention.

The agents useful in the present invention are members of the class of compounds known as thiazoliums, and in particular thiazolium compounds substituted with heterocyclic groups.

The agents comprise compounds having the following structural formula:

wherein $R^1$ and $R^2$ are independently selected from the group consisting of hydrogen and an alkyl group, optionally substituted by a hydroxy group;

Y is a group of the formula —$CH_2C(=O)R$ wherein R is a heterocyclic group other than alkylenedioxyaryl containing 4–10 ring members and 1–3 heteroatoms selected from the group consisting of oxygen, nitrogen and sulfur; said heterocyclic group optionally substituted by one or more substituents selected from the group consisting of alkyl, oxo, alkoxycarbonylalkyl, aryl, and aralkyl; and said one or more substituents optionally substituted by one or more alkyl or alkoxy groups; or a group of the formula —$CH_2C(=O)$—NHR' wherein R' is a heterocyclic group other than alkylenedioxyaryl containing 4–10 ring members and 1–3 heteroatoms selected from the group consisting of oxygen, nitrogen, and sulfur; said heterocyclic group optionally substituted by one or more alkoxycarbonylalkyl groups; and X is a halide, tosylate, methanesulfonate or mesitylenesulfonate ion.

The ability to reverse already-formed advanced glycosylation products carries with it significant implications in all applications where advanced glycation and concomitant molecular crosslinking is a serious detriment. In the area of food technology, for instance, the cleavage of cross-links would confer a reversal of the increased toughness resulting from the formation of AGEs during storage. In a preferred embodiment, the application of agents capable of reversal of the Maillard process has particular benefit in vivo as AGE cross-linking adversely affects several of the significant protein masses in the body, among them collagen, elastin, lens proteins, and the kidney glomerular basement membrane. These proteins deteriorate both with age (hence the application of the term "protein aging") and more rapidly as a consequence of diabetes. Accordingly, the ability to reverse the cross-linking of these proteins and thus to reduce the amount of cross-links present between advanced glycosylation end products and other proteins in the body carries the promise for treatment of the complications of diabetes and aging for instance, and thereby improving the quality and, perhaps, duration of animal and human life.

It is a yet further object of the present invention to provide agents which reverse the advanced glycosylation end products formed as a consequence of the aforesaid advanced glycosylation reaction sequence by cleaving the α-dicarbonyl-based protein crosslinks present in the advanced glycosylation end products.

It is a still further object of the present invention to provide therapeutic methods of treating the adverse consequences of molecular or protein aging by resort to the aforesaid method and agents to achieve the reversal or cleavage of cross-links derived from advanced glycosylation reactions.

It is a still further object of the present invention to provide compositions, including pharmaceutical compositions, incorporating the agents of the present invention.

Other objects and advantages will become apparent to those skilled in the art from a consideration of the ensuing description.

DETAILED DESCRIPTION OF THE INVENTION

In accordance with the present invention, agents, compositions including pharmaceutical compositions containing said agents and associated methods are described which reverse already-formed advanced glycosylation end product-derived cross-links (AGE cross-links). Useful agents, for instance, comprise compounds having the structural formula:

wherein $R^1$ and $R^2$ are independently selected from the group consisting of hydrogen and an alkyl group optionally substituted by a hydroxy group;

Y is a group of the formula —$CH_2C(=O)R$ wherein R is a heterocyclic group other than alkylenedioxyaryl containing 4–10 ring members and 1–3 heteroatoms selected from the group consisting of oxygen, nitrogen and sulfur; said heterocyclic group optionally substituted by one or more substituents selected from the group consisting of alkyl, oxo, alkoxycarbonylalkyl, aryl, and aralkyl groups; and said one or more substituents optionally substituted by one or more alkyl or alkoxy groups;

or a group of the formula —$CH_2C(=O)$—NHR' wherein R' is a heterocyclic group other than alkylenedioxyaryl containing 4–10 ring members and 1–3 heteroatoms selected from the group consisting of oxygen, nitrogen, and sulfur; said heterocyclic group optionally substituted by one or more alkoxycarbonylalkyl groups; and X is a halide, tosylate, methanesulfonate or mesitylenesulfonate ion.

The heterocyclic groups referred to herein include 4–8 membered rings having at least one and up to 3 heteroatoms, e.g., oxygen, nitrogen, or sulfur, therein, and including various degrees of unsaturation. Representatives of such heterocyclic groups are those such as isoxazolyl, phenylisoxazolyl, furanyl, morpholino, thiomorpholino, pyrimidinyl, piperidino, homopiperidino, piperazino, methylpiperazino, hexamethyleneimino, tetrahydroquinolyl, pyridyl, methylpyridyl, imidazolyl, pyrrolidinyl, 2,6-dimethylmorpholino, furfuryl, 1,2,4-triazoylyl, thiazolyl, thiophenyl, thiazolinyl, methylthiazolyl, and the like. Excluded are alkylenedioxyaryl substituents, which are described in copending application Ser. No. 08/588,249, incorporated herein by reference. The heterocyclic groups of the present invention may be further substituted, for example, by an oxo group, to form, for example, a 2-oxo-tetrahydroquinolinyl group, or substituted by one or more alkyl, alkoxycarbonylalkyl, aryl, or aralkyl groups, and such substituents may be further substituted by one or more alkyl or alkoxy groups.

Examples of Y groups of the compounds of the present include but are not limited to: 3-[2-(3-phenyl-5-isoxazolyl)-2-oxoethyl]; 3-(2-(4-morpholinyl)-2-oxoethyl); 3-[2-(2,6-dimethyl-4-morpholinyl)-2-oxoethyl]; 3-(2-(1-piperidinyl)-2-oxoethyl); 3-[2-(2-oxo-1,2,3,4-tetrahydro-6-quinolinyl)-2-oxoethyl]; 3-(2-(1-pyrrolidinyl)-2-oxoethyl; 3-[2-(3-methyl-2-thianaphthenyl)-2-oxoethyl]; 3-[2-(4-phenyl-1-piperazinyl)-2-oxoethyl; 3-(2-(2-thienyl)-2-oxoethyl); 3-(2-(2-thienyl)-2-oxoethyl); 3-(2-(4-thiomorpholinyl)-2-oxoethyl); 3-(2-(hexahydro-1-azepinyl)-2-oxoethyl); 3-[2-(4-[2-methoxyphenyl]-1-piperazinyl)-2-oxoethyl; 3-(2-(octahydro-1-azocinyl)-2-oxoethyl); 3-(2-(2-pyridinyl)-2-oxoethyl; 3-[2-(2-methyl-1-piperidinyl)-2-oxoethyl]; 3-[2-(2,6-dimethyl-1-piperidinyl)-2-oxoethyl; 3-[2-(4-benzyl-1-piperidinyl)-2-oxoethyl]; and 3-[2-(4-benzyl-1-piperazinyl)-2-oxoethyl].

The alkyl groups referred to above contain one to about eighteen carbon atoms and include, for example, methyl, ethyl, propyl, butyl, pentyl, hexyl, octyl, decyl, dodecyl, and octadecyl, and the corresponding branched-chain isomers thereof. The alkyl groups optionally substituted by hydroxy groups include alkyl groups as hereinbefore defined substituted with a hydroxy group at any position, such as but not limited to the following examples: hydroxymethyl, 1-hydroxyethyl, 2-hydroxyethyl, 1-hydroxypropyl, 2-hydroxypropyl, 3-hydroxypropyl, 6-hydroxyhexyl, and the like. Similarly, the alkoxy groups contain from one to about eighteen carbon atoms, and include, for example, methoxy, ethoxy, propoxy, butoxy, pentoxy, hexoxy, decoxy, and octadecoxy, and the corresponding branched-chain isomers thereof.

The alkoxycarbonylalkyl groups encompassed by the above formula include those wherein the alkoxy portion contain from one to about eighteen carbon atoms and the alkyl portion contains from 1 to about eighteen carbon atoms. Typical alkoxycarbonyl portions are those such as acetoxy or ethanoyloxy, propanoyloxy, butanoyloxy, pentanoyloxy, hexanoyloxy, decanoyloxy, and octadecanoyloxy, and the corresponding branched chain isomers thereof. Typical alkyl portions are as described hereinabove.

The aryl groups encompassed by the above formula are those containing 6–10 carbon atoms, such as naphthyl, phenyl and alkyl or alkoxy substituted-phenyl, e.g., toluyl and xylyl.

For the purposes of this invention, the compounds of the present invention are formed as biologically and pharmaceutically acceptable salts. Useful salt forms are the halides, particularly the bromide and chloride, tosylate, methanesulfonate, and mesitylenesulfonate salts. Other related salts can be formed using similarly non-toxic, and biologically and pharmaceutically acceptable anions.

Of the compounds encompassed herein, certain substituents are preferred. For instance, the compounds wherein $R_1$ or $R_2$ are hydrogen or alkyl groups are preferred. Also highly preferred are the compounds wherein Y is a 2-oxoethyl group with a heterocyclic group of thiophenyl, thiomorpholinyl, furanyl, 2-oxo-tetrahydroquinolinyl, and pyrrolidinyl.

As described in the formula above, the heterocyclic group may be represented by the R group of the formula —$CH_2C(=O)$—R, or it may represent the R' group of the formula —$CH_2C(=O)NHR'$. Representative, non-limiting examples of compounds of the present invention are:

3-[2-(3-phenyl-5-isoxazolyl)-2-oxoethyl]-thiazolium bromide

3-[2-(3-phenyl-5-isoxazolyl)-2-oxoethyl]-4,5-dimethylthiazolium bromide

3-[2-(3-phenyl-5-isoxazolyl)-2-oxoethyl]-4-methyl-5-(2-ydroxyethyl)-thiazolium bromide 3-[2-[4-(2-ethoxy-2-oxoethyl)-2-thiazolyl]amino-2-oxoethyl]-4,5-dimethyl-thiazolium chloride 3-[2-(3-phenyl-5-isoxazolyl)-2-oxoethyl]-4-methyl-5-(6-hydroxyhexyl)-thiazolium bromidehiazolium bromide 3-[2-(3-phenyl-5-isoxazolyl)-2-oxoethyl]-thiazolium bromide 3-(2-(1-piperidinyl)-2-oxoethyl)-4,5-dimethylthiazolium bromide 3-(2-(2-furanyl)-2-oxoethyl)-4,5-dimethylthiazolium bromide 3-(2-(2-furanyl)-2-oxoethyl)-4-(2-hydroxypentyl)thiazolium bromide 3-[2-(2-oxo-1,2,3,4-tetrahydro-6-quinolinyl)-2-oxoethyl]-4,5-dimethylthiazolium bromide 3-(2-(1-pyrrolidinyl)-2-oxoethyl)-4,5-dimethyl-thiazolium bromide 3-[2-(3-methyl-2-thianaphthenyl)-2-oxoethyl]-4,5-dimethylthiazolium bromide 3-[2-(4-phenyl-1-piperazinyl)-2-oxoethyl]-4,5-dimethylthiazolium bromide 3-(2-(2-thienyl)-2-oxoethyl)-4,5-dimethyl-thiazolium bromide 3-(2-(2-thienyl)-2-oxoethyl)-4-methyl-5-hydroxyethylthiazolium bromide 3-(2-(4-thiomorpholinyl)-2-oxoethyl)-4,5-dimethylthiazolium bromide 3-(2-(hexahydro-1-azepinyl)-2-oxoethyl)-4,5-dimethyl-thiazolium bromide 3-[2-(4-[2-methoxyphenyl]-1-piperazinyl)-2-oxoethyl]-4,5-dimethylthiazolium chloride 3-(2-(octahydro-1-azocinyl)-2-oxoethyl)-4,5-dimethyl-thiazolium bromide 3-(2-(2-pyridinyl)-2-oxoethyl)-4,5-dimethyl-thiazolium bromide 3-[2-(2-methyl-1-piperidinyl)-2-oxoethyl]-4,5-dimethylthiazolium chloride 3-[2-(2,6-dimethyl-1-piperidinyl)-2-oxoethyl]-4,5-dimethylthiazolium chloride 3-[2-(4-benzyl-1-piperidinyl)-2-oxoethyl]-4,5-dimethylthiazolium chloride 3-[2-(4-benzyl-1-piperazinyl)-2-oxoethyl]-4,5-dimethylthiazolium chloride 3-[2-(3-phenyl-5-isoxazolyl)-2-oxoethyl]-4-octylthiazolium bromide 3-(2-(4-morpholinyl)-2-oxoethyl)-4,5-dimethylthiazolium bromide 3-[2-[4-(2-ethoxy-2-oxoethyl)-2-thiazolyl]amino-2-oxoethyl]-4,5-dipropylthiazolium chloride 3-(2-(4-morpholinyl)-2-oxoethyl)-4,5-dioctadecylthiazolium bromide 3-[2-(2,6-dimethyl-4-morpholinyl)-2-oxoethyl]-4,5-dipentylthiazolium bromide 3-(2-(1-piperidinyl)-2-oxoethyl)-4,5-didodecylthiazolium bromide 3-(2-(2-furanyl)-2-oxoethyl)-5-decylthiazolium bromide 3-[2-(2-oxo-1,2,3,4-tetrahydro-6-quinolinyl)-2-oxoethyl]-4,5-dioctylthiazolium bromide 3-(2-(1-pyrrolidinyl)-2-oxoethyl)-4,5-diethylthiazolium bromide 3-[2-(3-methyl-2-thianaphthenyl)-2-oxoethyl]-4,5-dipentylthiazolium bromide 3-[2-(4-phenyl-1-piperazinyl)-2-oxoethyl]-thiazolium bromide 3-(2-(2-thienyl)-2-oxoethyl)-thiazolium bromide 3-(2-(2-thienyl)-2-oxoethyl)-4-methyl-5-(6-hydroxyhexyl)thiazolium bromide 3-(2-(4-thiomorpholinyl)-2-oxoethyl)thiazolium bromide 3-(2-(hexahydro-1-azepinyl)-2-oxoethyl)-4,5-dioctylthiazolium bromide 3-(2-(octahydro-1-azocinyl)-2-oxoethyl)-4,5-didecylthiazolium bromide 3-(2-(2-pyridinyl)-2-oxoethyl)-4,5-dioctylthiazolium bromide 3-[2-(2-methyl-1-piperidinyl)-2-oxoethyl]-4,5-dipropylthiazolium chloride 3-[2-(2,6-dimethyl-1-piperidinyl)-2-oxoethyl]-4-methylthiazolium chloride 3-[2-(4-benzyl-1-piperidinyl)-2-oxoethyl]-5-methylthiazolium chloride 3-[2-(4-benzyl-1-piperazinyl)-2-oxoethyl]-4-octylthiazolium chloride The above compounds are capable of reversing already-formed advanced glycosylation end products on proteins. The cross-linking of proteins by formation of advanced glycosylation end products contributes to the entrapment of other proteins and results in the development in vivo of conditions such as reduced elasticity and wrinkling of the skin, certain kidney diseases, atherosclerosis, osteoarthritis and the like. Similarly, foodstuffs including plant and animal material that undergoes nonenzymatic browning deteriorates and becomes spoiled or toughened and, consequently, inedible, unpalatable or non-nutritious. Thus, the compounds employed in accordance with this invention reduce the level of the advanced glycosylation end product-associated cross-links already present in the protein material.

The present methods and compositions hold the promise for reversing the aging of key proteins both in animals and plants, and concomitantly, conferring both economic and medical benefits as a result thereof. In the instance of foodstuffs, the administration of the present composition holds the promise for reversing the physico-chemical changes imparted to foodstuffs on storage, such as the increased toughness of meats that occurs during aging or storage.

The therapeutic implications of the present invention relate to the reversal of the aging process which has, as indicated earlier, been identified and exemplified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence and tend to occur at an accelerated rate in patients afflicted with diabetes mellitus as a consequence of their hyperglycemia. Thus, the present therapeutic method is relevant to treatment of these and related conditions in patients either of advanced age or those suffering from one of the mentioned pathologies.

Molecular cross-linking through advanced glycosylation product formation can decrease solubility of structural proteins such as collagen in vessel walls and can also trap serum proteins, such as lipoproteins to the collagen. Also, the presence of advanced glycosylation end products and associated cross-links may result in increased permeability of the endothelium and consequently covalent trapping of extravasated plasma proteins in subendothelial matrix, as well as a reduction in susceptibility of both plasma and matrix proteins to physiologic degradation by enzymes. For these reasons, the progressive occlusion of diabetic vessels induced by chronic hyperglycemia has been hypothesized to result from excessive formation of sugar-derived and particularly, glucose-derived cross-links. Such diabetic microvascular changes and microvascular occlusion can be effectively reversed by chemical reversal or cleavage of the advanced glycosylation product cross-link formation utilizing a composition and the methods of the present invention.

Certain of the compounds disclosed herein are novel:
wherein $R^1$ and $R^2$ are independently selected from the group consisting of hydrogen and an alkyl group, optionally substituted by a hydroxy group;
Y is a group of the formula —CH$_2$C(=O)R wherein R is a heterocyclic group other than alkylenedioxyaryl containing 4–10 ring members and one heteroatom selected from the group consisting of sulfur and nitrogen, or 2–3 heteroatoms selected from the group consisting of oxygen, nitrogen and sulfur; said heterocyclic group optionally substituted by one or more substituents selected from the group consisting of alkyl, oxo, alkoxycarbonylalkyl, aryl, and aralkyl groups; and said one or more substituents optionally substituted by one or more alkyl or alkoxy groups;
or a group of the formula —CH$_2$C(=O)—NHR' wherein R' is a heterocyclic group other than alkylenedioxyaryl containing 4–10 ring members and 1–3 heteroatoms selected from the group consisting of oxygen, nitrogen, and sulfur; said heterocyclic group optionally substituted by one or more alkoxycarbonylalkyl groups;
and X is a halide, tosylate, methanesulfonate or mesitylenesulfonate ion.

The heterocyclic groups referred to herein include 4–8 membered rings having at least one nitrogen or sulfur atom, or 4–8 membered rings having 2–3 heteroatoms, e.g., oxygen, nitrogen, or sulfur, therein; and including various degrees of unsaturation. Representatives of such heterocyclic groups are those such as isoxazolyl, phenylisoxazolyl, morpholino, thiomorpholino, pyrimidinyl, piperidino, homopiperidino, piperazino, methylpiperazino, hexamethyleneimino, tetrahydroquinolyl, pyridyl, methylpyridyl, imidazolyl, pyrrolidinyl, 2,6-dimethylmorpholino, furfuryl, 1,2,4-triazoylyl, thiazolyl, thiophenyl, thiazolinyl, methylthiazolyl, and the like. Excluded are alkylenedioxyaryl substituents, which are described in co-pending application Ser. No. 08/588,249, incorporated herein by reference. The heterocyclic groups of the present invention may be further substituted, for example, by an oxo group, to form, for example, a 2-oxo-tetrahydroquinolinyl group, or substituted by one or more alkyl, alkoxycarbonylalkyl, aryl, or aralkyl groups, and such substituents may be further substituted by one or more alkyl or alkoxy groups.

The alkyl groups, alkoxy groups, alkoxycarbonylalkyl groups, aryl groups, and salts are as described hereinabove.

As described in the formula above, the heterocyclic group may be represented by the R group of the formula —CH$_2$C(=O)—R, or it may represent the R' group of the formula —CH$_2$C(=O)NHR'. Representative examples of novel compounds of the present invention are:

3-[2-(3-phenyl-5-isoxazolyl)-2-oxoethyl]-thiazolium bromide

3-[2-(3-phenyl-5-isoxazolyl)-2-oxoethyl]-4,5-dimethylthiazolium bromide

3-[2-(3-phenyl-5-isoxazolyl)-2-oxoethyl]-4-methyl-5-(2-hydroxyethyl)-thiazolium bromide 3-[2-[4-(2-ethoxy-2-oxoethyl)-2-thiazolyl]amino-2-oxoethyl]-4,5-dimethylthiazolium chloride 3-(2-(4-morpholinyl)-2-oxoethyl)-4,5-dimethylthiazolium bromide 3-[2-(2,6-dimethyl-4-morpholinyl)-2-oxoethyl]-4,5-dimethylthiazolium bromide 3-(2-(1-piperidinyl)-2-oxoethyl)-4,5-dimethylthiazolium bromide 3-[2-(2-oxo-1,2,3,4-tetrahydro-6-quinolinyl)-2-oxoethyl]-4,5-dimethylthiazolium bromide 3-(2-(1-pyrrolidinyl)-2-oxoethyl)-4,5-dimethyl-thiazolium bromide 3-[2-(3-methyl-2-thianaphthenyl)-2-oxoethyl]-4,5-dimethylthiazolium bromide 3-[2-(4-phenyl-1-piperazinyl)-2-oxoethyl]-4,5-dimethylthiazolium bromide 3-(2-(2-thienyl)-2-oxoethyl)-4,5-dimethyl-thiazolium bromide 3-(2-(2-thienyl)-2-oxoethyl)-4-methyl-5-hydroxyethylthiazolium bromide 3-(2-(4-thiomorpholinyl)-2-oxoethyl)-4,5-dimethylthiazolium bromide 3-(2-(hexahydro-1-azepinyl)-2-oxoethyl)-4,5-dimethyl-thiazolium bromide 3-[2-(4-[2-methoxyphenyl]-1-piperazinyl)-2-oxoethyl]-4,5-dimethylthiazolium chloride 3-(2-(octahydro-1-azocinyl)-2-oxoethyl)-4,5-dimethylthiazolium bromide 3-(2-(2-pyridinyl)-2-oxoethyl)-4,5-dimethylthiazolium bromide 3-[2-(2-methyl-1-piperidinyl)-2-oxoethyl]-4,5-dimethylthiazolium chloride 3-[2-(2,6-dimethyl-1-piperidinyl)-2-oxoethyl]-4,5-dimethylthiazolium chloride 3-[2-(4-benzyl-1-piperidinyl)-2-oxoethyl]-4,5-dimethylthiazolium chloride 3-[2-(4-benzyl-1-piperazinyl)-2-oxoethyl]-4,5-dimethylthiazolium chloride As described in the Background section above, studies on other AGE cross-link cleavage agents have shown the ability to reverse cardiovascular damage in an experimental model of diabetes. As diabetes is often considered to be a model of accelerated aging, especially with respect to macrovascular complications, the agents of the present invention are suitable for therapeutic use in such complications of aging, examples of which are described above.

As will be shown in the Examples below, and as cited above, compounds capable of reversing AGE cross-links show significant promise in the treatment of various diseases and complications related to protein aging. Compounds active in an in vitro model of AGE cross-linking in which the compounds are evaluated for their ability to reverse the covalent cross-linking of IgG to red blood cell membranes, or cleave collage cross-links, has corresponding in-vivo activity in a model of protein aging. As described above, such studies demonstrate positive effects of such agents on cardiovascular complications related to aging which are accelerated in experimental diabetes (see Wolffenbuttel et al., 1998, "Breakers of Advanced Glycation End Products Restores Large Artery Properties in Experimental Diabetes," Proc. Nat. Acad. Sci. U.S.A. 95:4630–4634). In these studies, rats diabetic for 9 weeks followed by 1 to 3 weeks administration of an AGE breaker compound resulted in reversal of diabetes-induced increases in large artery stiffness. Parameters that were improved included cardiac output, peripheral resistance, systemic arterial compliance, input impedance of the aorta, and compliance of the carotid artery. Thus, active AGE-reversing compounds of the present invention are candidates for the treatment of the complications of protein aging.

In the instance where the compositions of the present invention are utilized for in vivo or therapeutic purposes, it may be noted that the compounds or agents used therein are biocompatible. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of the present invention may be utilized.

A liquid form would be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the agent in a suitable vehicle such as water, ethanol, propylene glycol, perhaps including a carrier to aid in penetration into the skin or eye. For example, a topical preparation could include up to about 10% of the compound of Formula I. Other suitable forms for administration to other body tissues are also contemplated.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 30 mg/kg.

The agent of the present invention is formulated in compositions in an amount effective to inhibit and reverse the formation of advanced glycosylation end products. This amount will, of course, vary with the particular agent being utilized and the particular dosage form, but typically is in the range of 0.01% to 1.0%, by weight, of the particular formulation.

The compounds of the present invention can be prepared generally according to the methods described in Potts et al., 1976, J. Org. Chem. 41:187, and Potts et al., 1977, J. Org. Chem. 42:1648, or as shown in the following scheme wherein R is a heterocyclic group, $R^1$, $R^2$, and Z are as described hereinabove, and X is a halogen atom:

(I) (II)

In the reaction scheme above, the appropriate substituted thiazole compounds of formula I is reacted with the appropriate halo compound of formula II, to afford the desired compound of the present invention; all substituents are as hereinbefore defined.

The halo reactant may be prepared by suitable techniques known in the art. For example, for the preparation of 3-(2-thiophenyl-2-oxoethyl)-4,5-dimethyl-thiazolium bromide, the reactant 2-bromothiophene is reacted with dimethylthiazole. 2-Bromothiophene may be prepared according to the method of King et al., 1964, J. Org. Chem. 29:3459, by the bromination of 2-acetylthiophene with copper (II) bromide. Specific methods are described in the examples below.

The conditions for the. reaction between the halo compound and the thiazole derivative generally involve refluxing the mixture at 110° C. in an oil bath for 3–7 hours with a minimum amount of solvent such as acetonitrile, or refluxing the mixture in ethanol or acetonitrile for 3–5 hours. If the halo reactant contains chlorine, the first condition is used. For a bromo compound, the second condition is preferable.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Preparation of 3-(2-thiophenyl-2-oxoethyl)-4,5-dimethyl-thiazolium bromide

This compound was prepared by reacting 4,5-dimethylthiazole with 2-bromoacetylthiophene. 2-Bromoacetylthiophene was prepared by bromination of 2-acetylthiophene with copper (II) bromide according to the method of King et al., 1964, J. Org. Chem. 29:3459. 2-Acetylthiophene (6 g, 47.6 mmol) was dissolved in chloroform (60 mL) and added to a slurry of copper (II) bromide (13.5 g, 60.44 mmol) in ethyl acetate (120 mL). The mixture was refluxed for 6 hours and then filtered while still hot through a celite pad. The filtrate cake was washed with ethyl acetate and the combined filtrate was evaporated to give 2-bromoacetylthiophene (9.5 g, 97.3%). The crude product was used directly in the next reaction.

A solution of 4,5-dimethylthiazole (2.2 g, 19.4 mmol) and 2-bromoacetylthiophene (4 g, 19.4 mmol) in ethyl alcohol (20 mL) was refluxed for 3 hours. It was cooled to room temperature and t-butyl methyl ether (10 mL) was added. The reaction mixture was left at room temperature overnight with stirring. The white product separated and was filtered and dried. It was crystallized from ethyl alcohol (4.42 g, 73%), m.p. 203–205° C.

EXAMPLE 2

Synthesis of 3-(2-pyrrolidinyl-2-oxoethyl)-4,5-dimethyl-thiazolium chloride 3-(2-pyrrolidinyl-2-oxoethyl)-4,5-dimethyl-thiazolium chloride was prepared from the reaction of N-(chloroacetyl)pyrrolidine with 4,5-dimethylthiazole. N-(chloroacetyl)pyrrolidine was prepared as follows. Pyrrolidine (63.9 g, 0.9 mol) was taken in methylene chloride (640 mL) and cooled to 0° C. in a salt-ice bath. To the stirred mixture was added chloroacetyl chloride (101.8 g in 450 mL of $CH_2Cl_2$, 0.9 mol) dropwise keeping the inside temperature below 15° C. After adding the chloroacetyl chloride, the mixture was stirred for an hour at 5° C. Sodium hydroxide solution (7 M, 190 mL) was added with vigorous stirring such that the inside temperature did not exceed 20° C. The mixture was stirred for 15 minutes and the aqueous layer was separated. The organic layer was washed successively with saturated sodium bicarbonate solutions (2×200 mL), water (1×200 mL) and dried over anhydrous sodium sulfate. The solvent was removed in vacuo and the residue was recrystallized from hexane to give 64.5 g (48.6%) of white plate crystals, m.p. 43° C.

A mixture of N-(chloroacetyl)pyrrolidine (37.3 g, 0.25 mol), 4,5-dimethylthiazole (28.69 g, 0.25 mol) and acetonitrile (17 mL) was refluxed in an oil bath at 105–110° C. for 7 hours. To the reaction mixture was added acetonitrile (230 mL) and continued to heat for 20 minutes, then t-butyl methyl ether (250 mL) was added. The reaction mixture was kept at room temperature overnight. The product was filtered and washed with a mixture of t-butyl methyl ether and acetonitrile (1:1 v/v, 100 mL), and t-butyl methyl ether (150 mL) to obtain 59.64 g (90.2% yield) of white solid. The crude product (59.64 g) was dissolved in acetonitrile (350 mL) with heating, filtered, t-butyl methyl ether (350 mL) added, and the solution was allowed to cool at room temperature for 3 hours. The product was filtered and washed with a mixture of t-butyl methyl ether and acetonitrile (1:1 v/v, 300 mL), and t-butyl methyl ether (300 mL) to yield 56.95 g (86.1% yield) of white crystals, m.p. 196–198° C.

EXAMPLE 3

Using the procedures described above in Examples 1 and 2, the following compounds were prepared using the corresponding reactants. The melting points are indicated.

| | |
|---|---|
| 3-[2-(3-phenyl-5-isoxazolyl)-2-oxoethyl]-thiazolium bromide | 213–214° C. |
| 3-[2-(3-phenyl-5-isoxazolyl)-2-oxoethyl]-4,5-dimethylthiazolium bromide | 245–246° C. (dec.) |
| 3-[2-(3-phenyl-5-isoxazolyl)-2-oxoethyl]-4-methyl-5-(2-hydroxyethyl)-thiazolium bromide | 209–210° C. (dec.) |
| 3-[2-[4-(2-ethoxy-2-oxoethyl)-2-thiazolyl]amino-2-oxoethyl]-4,5-dimethyl-thiazolium chloride | 120–121° C. |
| 3-(2-(4-morpholinyl)-2-oxoethyl)-4,5-dimethylthiazolium bromide | 197–198° C. (dec.) |
| 3-[2-(2,6-dimethyl-4-morpholinyl)-2-oxoethyl]-4,5-dimethylthiazolium bromide | 215–216° C. |
| 3-(2-(1-piperidinyl)-2-oxoethyl)-4,5-dimethylthiazolium bromide | 240–242° C. |
| 3-(2-(2-furanyl)-2-oxoethyl)-4,5-dimethylthiazolium bromide | 195–196° C. (dec.) |
| 3-[2-(2-oxo-1,2,3,4-tetrahydro-6-quinolinyl)-2-oxoethyl]-4,5-dimethylthiazolium bromide | 274–275° C. (dec.) |
| 3-(2-(1-pyrrolidinyl)-2-oxoethyl)-4,5-dimethyl-thiazolium chloride | 189–198° C. |
| 3-[2-(3-methyl-2-thianaphthenyl)-2-oxoethyl]-4,5-dimethylthiazolium bromide | 171–172° C. |
| 3-[2-(4-phenyl-1-piperazinyl)-2-oxoethyl]-4,5-dimethylthiazolium bromide | 150–152° C. |
| 3-(2-(2-thienyl)-2-oxoethyl)-4,5-dimethyl-thiazolium bromide | 203–205° C. |
| 3-(2-(2-thienyl)-2-oxoethyl)-4-methyl-5-hydroxyethylthiazolium bromide | 175–176° C. |
| 3-(2-(4-thiomorpholinyl)-2-oxoethyl)-4,5-dimethylthiazolium chloride | 232–233° C. (dec.) |
| 3-(2-(hexahydro-1-azepinyl)-2-oxoethyl)-4,5-dimethyl-thiazolium chloride | 218–219° C. (dec.) |
| 3-[2-(4-[2-methoxyphenyl]-1-piperazinyl)-2-oxoethyl]-4,5-dimethylthiazolium chloride | 215–216° C. (dec.) |
| 3-(2-(octahydro-1-azocinyl)-2-oxoethyl)-4,5-dimethyl-thiazolium chloride | 210–212° C. (dec.) |
| 3-(2-(2-pyridinyl)-2-oxoethyl)-4,5-dimethyl-thiazolium bromide | 178–179° C. |
| 3-[2-(2-methyl-1-piperidinyl)-2-oxoethyl]-4,5-dimethylthiazolium chloride | 220–221° C. (dec.) |
| 3-[2-(2,6-dimethyl-1-piperidinyl)-2-oxoethyl]-4,5-dimethylthiazolium chloride | 248–249° C. (dec.) |
| 3-[2-(4-benzyl-1-piperidinyl)-2-oxoethyl]-4,5-dimethylthiazolium chloride | 170–171° C. |
| 3-[2-(4-benzyl-1-piperazinyl)-2-oxoethyl]-4,5-dimethylthiazolium chloride | 180–182° C. |

EXAMPLE 4

A typical pharmaceutical dosage form is prepared as follows.

| | mg/tablet |
|---|---|
| Compound of the present invention | 50 |
| Starch | 50 |
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a 11/32" punch with a hardness of 4 kg. These tablets will disintegrate within a half hour according to the method described in USP XVI.

EXAMPLE 5

| Lotion: | mg/tablet |
|---|---|
| Compound of Formula I | 1.0 |
| Ethyl alcohol | 400.0 |
| Polyethylene glycol 400 | 300.0 |
| Hydroxypropyl cellulose | 5.0 |
| Propylene glycol | to make 1.0 g |

EXAMPLE 6

Reversing Age Cross-Links

The activity of the compounds of the present invention to reverse AGE cross-links was evaluated in an in-vitro model, as follows. Blood was collected from streptozotocin-diabetic rats (6 to 8 wk diabetic) in heparinized tubes, centrifuged at 2500×g for 15 min. at 40° C., and the plasma and buffy-coat layers aspirated off. The RBC were washed with PBS (ca. 5 ml PBS per ml blood) three times.

Test compounds were dissolved in PBS and the pH adjusted to 7.0, if necessary. Two hundred microliters of washed RBC were added to 2 mL of test compound solution, and the mixture was incubated overnight at 37° C. For a control, 200 µl of RBC was incubated in 2 mL of PBS.

After the overnight incubation, the reaction mixtures were centrifuged and the RBC pellets were washed three times with PBS, followed by diluting 1:30 in PBS. Immunoglobulin G (IgG) bound to the surface of the washed RBCs was then determined.

Assay for RBC-IgG: The assay is performed in a Multiscreen-HA, 0.45 µm cellulose mixed esters membrane-sealed 96 well plate (Millipore MAHAS45). The membranes are first wet by filling the wells with 100 uL PBS, and the wells emptied by applying a vacuum to the Millititer vacuum manifold. Three hundred uL of Superblock (pre-warmed to 37° C.) is then added to each well and incubated at 37° C. for one hour. The Superblock is then removed from the wells by application of vacuum, then the wells are washed once with 300 ul of PBS-Tween (0.05%) and three times with PBS. The vacuum is then turned off.

One hundred µl of PBS is then added to each well. Each RBC sample is gently vortexed, and 50 uL pipetted into the wells, in sextuplicate. The wells labeled A1–A3 are left for a reagent blank and wells A4–A6 reserved for an antibody blank. Vacuum is then applied to remove the buffer and the RBCs are washed once with PBS. Alkaline phosphatase-labeled rabbit-anti-rat IgG is diluted 1 to 25000 in PBS, and 50 µl is added to triplicate wells of each sample. PBS alone is added to the other three wells of each sample. These will serve as sample blanks to adjust for any endogenous alkaline phosphatase activity. The samples are allowed to stand at room temperature for two hours. The solution is then removed by application of vacuum and the red blood cells are washed with PBS-Tween twice, PBS twice and with TBS twice. The bottom of the plate is rinsed with distilled water and blotted dry with paper towels. To each well is then added 100 µl of p-nitrophenyl phosphate substrate (1 mg/ml in diethanolamine buffer pH 9.5), and the color is allowed to develop for two hours at 37° C. The solutions in each well are then transferred to a 96 well microtiter plate inside the vacuum manifold. One hundred µl of PBS to each well and vacuum applied again to transfer any remaining solution into the microtiter plate. The OD at 410 nm is then read in a Dynatech Plate reader (Sample filter 1 and Ref. filter 4).

For data analysis, breaking activity (percent reversal) is expressed as the percent decrease in O.D. caused by incubation of RBC with the test compound compared to RBC incubated in PBS alone. Using the above assay, the following data was generated on the compounds of the present invention:

| Compound | Percent reversal |
|---|---|
| 3-(2-(2-thienyl)-2-oxoethyl)-4-methyl-5-hydroxyethylthiazolium bromide | 24% |
| 3-(2-(2-pyridinyl)-2-oxoethyl)-4,5-dimethyl-thiazolium bromide | 27% |
| 3-(2-(1-piperidinyl)-2-oxoethyl)-4,5-dimethylthiazolium bromide | 37% |
| 3-[2-(2,6-dimethyl-4-morpholinyl)-2-oxoethyl]-4,5-dimethylthiazolium bromide | 38% |
| 3-[2-(3-phenyl-5-isoxazolyl)-2-oxoethyl]-thiazolium bromide | 38% |
| 3-(2-(4-thiomorpholinyl)-2-oxoethyl)-4,5-dimethylthiazolium bromide | 47% |
| 3-(2-(2-thienyl)-2-oxoethyl)-4,5-dimethyl-thiazolium bromide | 53% |
| 3-(2-(1-pyrrolidinyl)-2-oxoethyl)-4,5-dimethyl-thiazolium bromide | 63% |
| 3-(2-(2-furanyl)-2-oxoethyl)-4,5-dimethylthiazolium bromide | 76% |
| 3-[2-(4-benzyl-1-piperidinyl)-2-oxoethyl]-4,5-dimethylthiazolium chloride | 70% |
| 3-[2-(2-oxo-1,2,3,4-tetrahydro-6-quinolinyl)-2-oxoethyl]-4,5-dimethylthiazolium bromide | 84% |

EXAMPLE 7

Reversing Collagen Cross-Links

In a further evaluation of the ability of compounds of the present invention to reverse AGE cross-links between a circulating protein and collagen, AGE-BSA was cross-linked to rat tail tendon collagen (type 1)-coated 96 well microtiter plates, and reversal of cross-linking was determined.

AGE-BSA preparation. AGE-BSA is prepared by incubation of a solution of BSA (400 mg/ml) in 0.4 M sodium phosphate buffer pH 7.4 with an equal volume of 400 mM glucose solution in the same buffer at 37° C. for 12 weeks. The pH of the incubation mixture is monitored weekly and adjusted to pH 7.4 if necessary. After 12 weeks, the AGE-BSA solution is dialyzed against PBS for 48 hours with 4 buffer changes. Protein concentration is determined by the micro-Lowry method.

Assay protocol. A Biocoat (Collaborative Biomedical Products) plate is blocked with Superblock (300 mL/well) at 37° C. for 1 hr and washed with PBS-Tween three times. AGE-BSA was diluted in PBS to a concentration required to obtain maximum cross-linking as determined in a preliminary experiment. One hundred µl of the AGE-BSA working solution is added to test wells and a similar concentration of BSA is added to blank wells. The first three wells are left empty for the reagent blank. The plate is incubated at 37° C. for four hours and washed with PBS-Tween three times.

Test compounds are dissolved in PBS and pH adjusted to 7.0 if necessary. One hundred µl of a test compound is added to triplicate wells. To measure maximum crosslinking 100 µl of PBS is added to three to six wells. The test compounds and PBS are also added to triplicate wells incubated with BSA, to obtain the blank readings. The plate is then incubated overnight at 37° C.

The plate is washed with PBS-Tween, 50 mL of Rabbit-anti-BSA antibody (1 to 4000 in PBS) is added to each well and the plate is incubated at room temperature for 60 min. After the plate is washed with PBS-Tween, 50 mL of horseradish peroxidase-conjugated-goat-anti-rabbit IgG (1 to 4000 in PBS) is added to each well except the first three wells. The plate is incubated at room temperature for 30 min. and washed with PBS-Tween. Two hundred µl of ABTS substrate (prepared from HRP-substrate buffer 10×(Sigma) diluted 1:10 in deionized water and mixed with 50× ABTS reagent (Sigma)) is added to each well and color developed at 37° C. for 15 min. Optical density is read at 410 nm with the sample filter set to "1" and the reference filter set to "5" on the Dynatech ELISA plate reader.

Data Analysis: The average optical density (OD) is calculated for each triplicate determination: Corrected OD= (Average of OD AGE-BSA wells–Average of OD BSA wells). Percent breaking by test compounds is expressed as the percent decrease in OD of TTC-AGE-BSA wells incubated with test compounds compared to TTC-AGE-BSA wells incubated with PBS.

Using the procedure above, it was found that 3 mM 3-[2-(3-phenyl-5-isoxazolyl)-2-oxoethyl]-thiazolium bromide caused a 15% reversal of AGE cross-links.

This invention may be embodied in other forms or carried out in other ways without departing from the spirit or essential characteristics thereof The present disclosure is therefore to be considered as in all respects illustrative and not restrictive, the scope of the invention being indicated by the appended claims, and all changes which come within the meaning and range of equivalency are intended to be embraced therein.

Various citations to the literature are presented herein, all of which are incorporated herein in their entireties.

What is claimed is:

1. A method of treating or reducing progression of (i) hypertension or (ii) the incidence of pathologies involving the entrapment of proteins by cross-linked target proteins in an animal, comprising administering to the animal an effective amount of composition comprising a compound selected from the group consisting of compounds of the formula

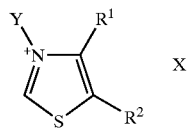

wherein $R^1$ and $R^2$ are independently selected from the group consisting of hydrogen and an alkyl group, which can be substituted by a hydroxy group;

Y is a
group of the formula —CH$_2$C(=O)R wherein R is a heterocyclic group other than alkylenedioxyaryl containing 4–10 ring members and 1–3 heteroatoms selected from the group consisting of oxygen, nitrogen and sulfur, the heterocyclic group can be substituted by one or more substituents selected from the group consisting of alkyl, oxo, alkoxycarbonylalkyl, aryl, and aralkyl groups; and said one or more substituents can be substituted by one or more alkyl or alkoxy groups; or a group of the formula —CH$_2$C(=O)R—NHR' wherein $R^1$ is a heterocyclic group other than alkylenedioxyaryl containing 4–10 ring members and 1–3 heteroatoms selected from the group consisting of oxygen, nitrogen, and sulfur, the heterocyclic group can be substituted by one or more alkoxycarbonylalkyl groups;

X is a pharmaceutically acceptable ion; and a carrier therefor.

2. The method of claim 1 comprising administering the composition wherein Y is a group of the formula —CH$_2$C(=O)R and wherein the alkyl, alkylene and alkoxy groups comprise up to six carbons.

3. The method of claim 1, comprising administering the composition wherein the heterocyclic group is azepinyl, azocinyl, hexamethyleneimino, imidazolyl, isoxazolyl, phenylisoxazolyl, morpholinyl, thiomorpholinyl, piperidinyl, homopiperidinyl, piperazinyl, pyridyl, pyrimidinyl, tetrahydroquinolyl, pyrrolidinyl, thiazolyl, thiazolinyl, thienyl, thiodiphenyl thiophenyl, or 1,2,4-triazoylyl.

4. The method of claim 1 comprising administering the composition wherein Y is selected from the group consisting of 3-[2-(3-phenyl-5-isoxazolyl)-2-oxoethyl]; 3-(2-(4-morpholinyl)-2-oxoethyl); 3-[2-(2,6-dimethyl-4-morpholinyl)-2-oxoethyl]; 3-(2-(1-piperidinyl)-2-oxoethyl); 3-[2-(2-oxo-1,2,3,4-tetrahydro-6-quinolinyl)-2-oxoethyl]; 3-(2-(1-pyrrolidinyl)-2-oxoethyl; 3-[2(3-methyl-2-thianaphthenyl)-2-oxoethyl]; 3-[2-(4-phenyl-1-piperazinyl)-2-oxoethyl]; 3-(2-(2-thienyl)-2-oxoethyl); 3-(2-(2-thienyl)-2-oxoethyl); 3-(2-(4-thiomorpholinyl)-2-oxoethyl); 3-(2-(hexahydro-1-azepinyl)-2-oxoethyl); 3-[2-(4-[2-methoxyphenyl]-1-piperazinyl)-2-oxoethyl]; 3-(2-(octahydro-1-azocinyl)-2-oxoethyl); 3-(2-(2-pyridinyl)-2-oxoethyl; 3-[2-(2-methyl-1-piperidinyl)-2-oxoethyl]; 3-[2-(2,6-dimethyl-1-piperidinyl)-2-oxoethyl; 3-[2-(4-benzyl-1-piperidinyl)-2-oxoethyl]; and 3-[2-(4-benzyl-1-piperazinyl)-2-oxoethyl].

5. The method of claim 4 comprising administering the composition wherein said compound is a 3-[2-(3-phenyl-5-isoxazolyl)-2-oxoethyl]-thiazolium, 3-[2-(3-phenyl-5-isoxazolyl)-2-oxoethyl]-4,5-dimethylthiazolium, 3-[2-(3-phenyl-5-isoxazolyl)-2-oxoethyl]-4-methyl-5-(2-hydroxyethyl)-thiazolium, 3-(2-(4-morpholinyl)-2-oxoethyl)-4,5-dimethylthiazolium, 3-(2-(1-piperidinyl)-2-oxoethyl)-4,5-dimethylthiazolium, 3-[2-(2-oxo-1,2,3,4-tetrahydro-6-quinolinyl)-2-oxoethyl]-4,5-dimethylthiazolium, 3-(2-(1-pyrrolidinyl)-2-oxoethyl)-4,5-dimethyl-thiazolium, 3-[2-(4-methyl-2-thianaphthenyl)-2-oxoethyl]-4,5-dimethylthiazolium, 3-[2-(4-phenyl)-1-piperazinyl)-2-oxoethyl]-4,5-dimethylthiazolium, 3-(2-(2-thienyl)-2-oxoethyl)-4,5-dimethyl-thiazolium, 3-(2-(2-thienyl)-2-oxoethyl)-4-methyl-5-hydroxyethylthiazolium, 3-(2-(4-thiomorpholinyl)-2-oxoethyl)-4,5-dimethylthiazolium, 3-(2-(hexahydro-1-azepinyl)-2-oxoethyl)-4,5-dimethyl-thiazolium, 3-[2-(4-[2-methoxyphenyl]-1-piperazinyl)-2-oxoethyl]-4,5-dimethylthiazolium, 3-(2-(octahydro-1-azocinyl)-2-oxoethyl)-4,5-dimethylthiazolium, 3-(2-(2-pyridinyl)-2-oxoethyl)-4,5-dimethyl-thiazolium, 3-[2-(2-methyl-1-piperidinyl)-2-oxoethyl]-4,5-dimethylthiazolium, 3-[2-(2,6-dimethyl-1-piperidinyl)-2-oxoethyl)-4,5-dimethylthiazolium, 3-[2-(4-benzyl-1-piperidinyl)-2-oxoethyl]-4,5-dimethylthiazolium, or 3-[2-(4-benzyl-1-piperazinyl)-2-oxoethyl]-4,5-dimethyl-thiazolium.

6. The method of claim 1 comprising administering the composition wherein said compound has the formula wherein Y is a group of the formula —CH$_2$C(=O)R—NHR' and wherein the alkyl, alkylene and alkoxy groups comprise up to six carbons.

7. The method of claim 6 comprising administering the composition wherein said compound is 3-[2-[4-(2-ethoxy-2-oxoethyl )-2-thiazolyl]amino-2-oxoethyl]-4,5-dimethyl-thiazolium chloride or another biologically acceptable salt thereof.

8. The method of claim 1, wherein the method is applied to treat or reduce progression of (i) hypertension.

9. The method of claim 8, comprising administering the composition wherein Y is a group of the formula —CH₂C(=O)R and wherein the alkyl, alkylene and alkoxy groups comprise up to six carbons.

10. The method of claim 8, comprising administering the composition wherein the heterocyclic group is azepinyl, azocinyl, hexamethyleneimino, imidazolyl, isoxazolyl, phenylisoxazolyl, morpholinyl, thiomorpholinyl, piperidinyl, homopiperidinyl, piperazinyl, pyridyl, pyrimidinyl, tetrahydroquinolyl, pyrrolidinyl, thiazolyl, thiazolinyl, thienyl, thionapthenyl thiophenyl, or 1,2,4-triazoylyl.

11. The method of claim 10, comprising administering the composition wherein Y is selected from the group consisting of 3-[2-(3-phenyl-5-isoxazolyl)-2-oxoethyl]; 3-(2-(4-morpholinyl)-2-oxoethyl); 3-[2-(2,6-dimethyl-4-morpholinyl)-2-oxoethyl]; 3-(2-(1-piperidinyl)-2-oxoethyl); 3-[2-(2-oxo-1,2,3,4-tetrahydro-6-quinolinyl)-2-oxoethyl]; 3-(2-pyrrolidinyl)-2-oxoethyl; 3-[2-(3-methyl-2-thianaphthenyl)-2-oxoethyl]; 3-[2-(4-phenyl-1-piperazinyl)-2-oxoethyl]; 3-(2-(2-thienyl)-2-oxoethyl); 3-(2-(2-thienyl)-2-oxoethyl); 3-(2-(4-thiomorpholinyl)-2-oxoethyl); 3-(2-(hexahydro-1-azepinyl)-2-oxoethyl); 3-[2-(4-]2-methoxyphenyl]-1-piperazinyl)-2-oxoethyl; 3-(2-(octahydro-1-azocinyl)-2-oxoethyl); 3-(2-(2-pyridinyl)-2-oxoethyl; 3-[2-(2-methyl-1-piperidinyl)-2-oxoethyl]; 3-[2-(2,6-dimethyl-1-piperidinyl)-2-oxoethyl; 3-[2-(4-benzyl-1-piperidinyl)-2-oxoethyl]; and 3-[2-(4-benzyl-1-piperazinyl)-2-oxoethyl].

12. The method of claim 11, comprising administering the composition wherein said compound is a 3-[2-(3-phenyl-5-isoxazolyl)-2-oxoethyl]thiazolium, 3-[2-(3-phenyl -5-isoxazolyl) -2-oxoethyl]4,5-dimethylthiazolium, 3-[2-(3-phenyl-5-isoxazolyl)-2-oxoethyl]-4-methyl-5-(2-hydroxyethyl)-thiazolium, 3-(2-(4-morpholinyl)-2-oxoethyl)-4,5-dimethylthiazolium, 3-[2-(2,6-dimethyl-4-morpholinyl)-2-oxoethyl]-4,5-dimethylthiazolium, 3-(2-(1-piperidinyl)-2-oxoethyl)-4,5-dimethylthiazolium, 3-[2-(2-oxo-1,2,3,4-tetrahydro-6-quinolinyl)-2-oxoethyl ]-4,5-dimethylthiazolium, 3-(2-(1-pyrrolidinyl)-2-oxoethyl)-4,5-dimethyl-thiazolium, 3-[2-(2-methyl-thianaphthenyl)-2-oxoethyl]-4,5-dimethylthiazolium, 3-(2-(4phenyl-1-piperazinyl)-2-oxoethyl)-4,5dimethylthiazolium, 3-(2-(2-thienyl)-2oxoethyl)-4,5-dimethyl-thiazolium,3-(2-(2-thienyl)-2-oxoethyl)-4-methyl-5-hydroxyethylthiazolium, 3-(2-4-thiomorpholinyl)-2-oxoethyl]-4,5-dimethylthiazolium,3-(2-(hexahydro-1-azepinyl)-2-oxoethyl)-4,5-dimethylthiazolium, 3-[2-(4-[2-methoxyphenyl]-1-piperazinyl)2-oxoethyl]-4,5-dimethylthiazolium, 3-(2-(octahydro-1-azocinyl)-2-oxoethyl)-4,5-dimethylthiazolium, 3-(2-(2-pyridinyl)-2-oxoethyl)-4,5-dimethyl-thiazolium,3-[2-(2-methyl-1-piperidinyl)-2-oxoethyl]-4,5-dimethylthiazolium, 3-[2-(2,6-dimethyl-1-piperidinyl)-2-oxoethyl]-4,5-dimethylthiazolium, 3-[2-(4-benzyl-1-piperazinyl)-2-oxoethyl]-4,5-dimethylthiazolium, or 3-[2-(4-benzyl-1-piperazinyl)-2-oxoethyl]-4,5-dimethylthiazolium.

13. The method of claim 8, comprising administering the composition wherein said compound has the formula wherein Y is a group of the formula —CH₂C=O)R—NHR' and wherein the alkyl, alkylene and alkoxy groups comprise up to six carbons.

14. The method of claim 13, comprising administering the composition wherein said compound is 3-[2-[4-(2-ethoxy-2-oxoethyl)-2-thiazolyl]amino-2-oxoethyl]-4,5-dimethyl-thiazolium chloride or another biologically acceptable salt thereof.

15. The method of claim 1, wherein the method is applied to treat or reduce progression of (ii) the incidence of pathologies involving the entrapment of proteins by cross-linked target proteins in an animal.

16. The method of claim 15, comprising administering the composition wherein Y is a group of the formula —CH₂C(=O)R and wherein the alkyl, alkylene and alkoxy groups comprise up to six carbons.

17. The method of claim 15, comprising administering the composition wherein the heterocyclic group is azepinyl, azocinyl, hexamethyleneimino, imidazolyl, isoxazolyl, phenylisoxazolyl, morpholinyl, thiomorpholinyl, piperidinyl, homopiperidinyl, piperazinyl, pyridyl, pyrimidinyl, tetrahydroquinolyl, pyrrolidinyl, thiazolyl, thiazolinyl, thienyl, thionapthenyl thiophenyl, or 1,2,4-triazoylyl.

18. The method of claim 17, comprising administering the composition wherein Y is selected from the group consisting of 3-[2-(3phenyl-5-isoxazolyl)-2-oxoethyl]; 3-(2-(4-morpholinyl)2-oxoethyl); 3-[2-(2,6-dimethyl-4-morpholinyl)-2-oxoethyl]; 3-(2-(1-piperidinyl)-2-oxoethyl); 3-[2-oxo-1,2,3,4-tetrahydro-6-quinolinyl)-2-oxoethyl]; 3-(2-(1-pyrrolidinyl)-2-oxoethyl; 3-[2-(3-methyl-2-thianaphthenyl)-2-oxoethyl]; 3-[2-(4-phenyl-1-piperazinyl)-2-oxoethyl]; 3-(2-(2-thienyl)-2-oxoethyl); 3-(2-(2-thienyl)-2-oxoethyl); 3-(2-(4-thiomorpholinyl)-2-oxoethyl); 3-(2-(hexahydro-1-azepinyl)-2-oxoethyl); 3-[2-(4-[2-methoxyphenyl]-1-piperazinyl)-2-oxoethyl; 3-(2-(octahydro-1-azocinyl)-2-oxoethyl); 3-(2-(2-pyridinyl)-2-oxoethyl; 3-[2-(2-methyl-1-piperidinyl)-2-oxoethyl]; 3-[2-(2,6-dimethyl-1-piperidinyl)-2-oxoethyl; 3-[2-(4-benzyl-1-piperidinyl)-2-oxoethyl]; and 3-[2-(4-benzyl-1-piperazinyl)-2-oxoethyl].

19. The method of claim 18, comprising administering the composition wherein said compound is a 3-[2-(3-phenyl-5-isoxazolyl)-2-oxoethyl]-thiazolium, 3-[2-(3-phenyl -5-isoxazolyl)-2-oxoethyl]-1-4,5-dimethylthiazolium, 3-[2-(3-phenyl-5-isoxazolyl)-2-oxoethyl]-4-methyl-5-(2-hydroxyethyl)-thiazolium, 3-(2-(4-morpholinyl)-2-oxoethyl)-4,5-dimethylthiazolium, 3-[2-(2,6-dimethyl-4-morpholinyl)-2-oxoethyl]-4,5-dimethylthiazolium, 3-(2-(1-piperidinyl)-2-oxoethyl)-4,5-dimethylthiazolium, 3-[2-(2-oxo-1,2,3,4-tetrahydro-6-quinolinyl)-2-oxoethyl[-4,5-dimethylthiazolium, 3-(2-(1-pyrrolidinyl)-2-oxoethyl)-4,5-dimethyl-thiazolium, 3-[2-(3-methyl-2-thianaphthenyl)-2-oxoethyl]-4,5-dimethylthiazolium, 3-[2-(4-phenyl-1-1-piperazinyl)-2-oxoethyl]-4,5-dimethylthylthiazolium, 3-(2-(2-thienyl)-2-oxoethyl)-4,5-dimethyl-thiazolium, 3-(2-(2-thienyl)-2-oxoethyl)-4-methyl-5-hydroxyethylthiazolium, 3-(2-(4-thiomorpholinyl)-2oxoethyl)-4,5-dimethylthiazolium, 3(2-(hexahydro-1-azepinyl)-2-oxoethyl)-4,5-dimethyl-thiazolium, 3-[2-(4-methoxyphenyl]-1-piperazinyl)-2-oxoethyl]-4,5-dimethylthiazolium, 3-(2-(octahydro-1azocinyl)-2-oxoethyl)-4,5-dimethylthiazolium, 3-(2-(2-pyridinyl)-2-oxoethyl)-4,5-dimethyl-thiazolium, 3-[2-(2-methyl-1-piperidinyl)-2-oxoethyl]-4,5-dimethylthiazolium, 3-[2-(2,6-dimethyl-1-piperidinyl)-2-oxoethyl]-4,5-dimethylthiazolium, 3-[2-(4-benzyl-1-piperidinyl)-2-oxoethyl]-4,5dimethylthiazolium, or 3-[2-(4-benzyl-1-piperazinyl)-2-oxoethyl]-4,5-dimethylthiazolium.

20. The method of claim 15, comprising administering the composition wherein said compound has the formula wherein Y is a group of the formula —CH₂C(=O)R—NHR' and wherein the alkyl, alkylene and alkoxy groups comprise up to six carbons.

21. The method of claim 20, comprising administering the composition wherein said compound is 3-[2-[4-(2-ethoxy-2-oxoethyl)-2-thiazolyl]amino-2-oxoethyl]-4,5-dimethyl-thiazolium chloride or another biologically acceptable salt thereof.

* * * * *